(12) United States Patent
Porrata et al.

(10) Patent No.: US 7,476,207 B2
(45) Date of Patent: *Jan. 13, 2009

(54) CONFIGURABLE APPARATUS AND METHOD FOR TREATING CARPAL TUNNEL SYNDROME

(75) Inventors: Humberto Luis Porrata, Wellington, FL (US); Alejandro Alberto Porrata, Miami, FL (US)

(73) Assignee: Porrata Group LLC, Miami, FL (US)

( * ) Notice: Subject to any disclaimer, the term of this patent is extended or adjusted under 35 U.S.C. 154(b) by 955 days.

This patent is subject to a terminal disclaimer.

(21) Appl. No.: 10/228,738

(22) Filed: Aug. 27, 2002

(65) Prior Publication Data

US 2003/0130691 A1    Jul. 10, 2003

Related U.S. Application Data

(60) Provisional application No. 60/315,152, filed on Aug. 27, 2001.

(51) Int. Cl.
*A61F 5/00* (2006.01)
(52) U.S. Cl. .............................. 602/13; 602/20; 602/21
(58) Field of Classification Search ...................... 602/5, 602/13, 20–22; 128/877–879
See application file for complete search history.

(56) References Cited

U.S. PATENT DOCUMENTS

| | | | |
|---|---|---|---|
| 2,388,330 A | | 11/1945 | Jungmann |
| 2,823,668 A | * | 2/1958 | Van Court et al. .............. 602/13 |
| 2,943,859 A | | 7/1960 | Koski |
| 4,067,063 A | | 1/1978 | Ettinger |

(Continued)

FOREIGN PATENT DOCUMENTS

DE    9200425    2/1991

(Continued)

*Primary Examiner*—Michael A. Brown
(74) *Attorney, Agent, or Firm*—Bryan Cave LLP; Daniel A. Crowe; Allan Watts

(57) ABSTRACT

The apparatus of the present invention stretches the carpal ligament and the flexor retinaculum, as well as the superficial structures and muscles of the hand, in a safe manner under precise control of the patient or a healthcare professional. A first embodiment of the inventive apparatus includes a housing for receiving the patient's hand with a bottom portion having a first pressure element positioned to contact the hypothenar region of the patient's hand and a second pressure element positioned to contact the thenar region of the patient's hand, and a top portion having a central longitudinal pressure element positioned to contact the central longitudinal dorsal region of the patient's hand. The first and second pressure elements are connected to active pressure sources (or source), such that when the hand is inserted into the housing, the first and second pressure elements are activated and exert pressure on the respective hypothenar and thenar regions of the hand while the central dorsal portion of the hand presses against the third pressure element. This forces the thenar and hypothenar regions apart thus advantageously stretching the carpal ligament, the flexor retinaculum, and superficial structures and muscles of the hand. In another embodiment of the present invention, the third pressure element is also connected to an active pressure source, such that active pressure is applied to the central dorsal region of the hand, while the first and second pressure elements apply pressure to the hypothenar and thenar regions of the hand.

5 Claims, 1 Drawing Sheet

U.S. PATENT DOCUMENTS

| | | | |
|---|---|---|---|
| 4,378,009 A | 3/1983 | Rowley et al. | |
| 4,382,439 A | 5/1983 | Shen | |
| 4,479,648 A | 10/1984 | Alivo | |
| 4,765,319 A | 8/1988 | Finnieston et al. | |
| 4,787,376 A | 11/1988 | Eisenberg | |
| 4,854,309 A | 8/1989 | Elsey | |
| 4,899,763 A | 2/1990 | Sebastian | |
| 4,941,460 A | 7/1990 | Working | |
| 5,014,689 A | 5/1991 | Meunchen et al. | |
| 5,029,573 A | 7/1991 | Chow | |
| 5,152,302 A | 10/1992 | Fareed | |
| 5,256,136 A | 10/1993 | Sucher | |
| 5,279,545 A | 1/1994 | Reese, Sr. | |
| 5,297,541 A | 3/1994 | Hensey | |
| 5,366,436 A | 11/1994 | Gibney | |
| 5,385,537 A | 1/1995 | Davini | |
| 5,405,357 A | 4/1995 | Rowe-Lanzisera et al. | |
| 5,413,553 A | 5/1995 | Downes | |
| 5,417,645 A | 5/1995 | Lemmen | |
| 5,427,577 A | 6/1995 | Picchietti | |
| 5,438,726 A | 8/1995 | Leite | |
| 5,441,058 A * | 8/1995 | Fareed | 128/898 |
| 5,468,220 A * | 11/1995 | Sucher | 602/21 |
| 5,584,854 A | 12/1996 | Minarik | |
| 5,613,941 A | 3/1997 | Prengler | |
| 5,647,850 A | 7/1997 | Allen | |
| 5,672,150 A | 9/1997 | Cox | |
| 5,702,355 A | 12/1997 | Repice et al. | |
| 5,707,345 A | 1/1998 | Fulk | |
| 5,810,753 A | 9/1998 | Eberbach | |
| 5,897,549 A * | 4/1999 | Tankovich | 606/9 |
| 5,916,185 A | 6/1999 | Chitwood | |
| 5,916,187 A | 6/1999 | Brill | |
| 5,925,007 A | 7/1999 | Ashline | |
| 5,950,628 A * | 9/1999 | Dunfee | 128/874 |
| 5,987,705 A * | 11/1999 | Reynolds | 16/431 |
| 6,029,277 A | 2/2000 | Picchione, II | |
| 6,120,472 A | 9/2000 | Singer, Jr. | |
| 6,146,347 A * | 11/2000 | Porrata | 602/21 |
| 6,179,800 B1 * | 1/2001 | Torrens | 602/21 |
| 6,200,286 B1 * | 3/2001 | Zamani | 602/64 |
| 6,213,969 B1 | 4/2001 | MacMorran et al. | |
| 6,217,536 B1 | 4/2001 | Gustafson | |
| 6,264,621 B1 | 7/2001 | Paske | |
| 6,290,662 B1 | 9/2001 | Morris et al. | |
| 6,953,440 B2 | 10/2005 | Porrata et al. | |
| 2002/0072786 A1 | 6/2002 | Gordon | |
| 2003/0018286 A1 | 1/2003 | Porrata | |
| 2003/0028136 A1 | 2/2003 | Stager | |
| 2003/0125652 A1 | 7/2003 | Porrata | |
| 2003/0125690 A1 | 7/2003 | Porrata | |
| 2003/0125691 A1 | 7/2003 | Porrata | |
| 2003/0130604 A1 | 7/2003 | Porrata | |
| 2003/0130652 A1 | 7/2003 | Porrata | |
| 2003/0130690 A1 | 7/2003 | Porrata | |
| 2003/0130691 A1 | 7/2003 | Porrata | |
| 2003/0130692 A1 | 7/2003 | Porrata | |

FOREIGN PATENT DOCUMENTS

| | | |
|---|---|---|
| EP | 0 861 651 A1 | 9/1998 |
| FR | 2650175 | 12/1991 |
| WO | WO 97 23176 A | 7/1997 |

* cited by examiner

CONFIGURABLE APPARATUS AND METHOD FOR TREATING CARPAL TUNNEL SYNDROME

This application claims the benefit of U.S. Provisional Application Ser. No. 60/315,152, filed Aug. 27, 2001. This application is related to four concurrently filed co-pending patent applications, namely U.S. Ser. No. 10/228,395, entitled Non-Invasive Apparatus and Method for Treating Carpal Tunnel Syndrome, U.S. Ser. No. 10/228,739, entitled Adjustable Apparatus and Method for Treating Carpal Tunnel Syndrome, U.S. Ser. No. 10/229,230, entitled Adaptable Apparatus and Method for Treating Carpal Tunnel Syndrome, U.S. Ser. No. 10/228,899, entitled Automatic Apparatus and Method for Treating Carpal Tunnel Syndrome, as well as co-pending patent application U.S. Ser. No. 10/199,747, entitled Apparatus and Method for Treating Carpal Tunnel Syndrome, filed Jul. 18, 2002, the contents of which are all hereby incorporated herein by reference.

FIELD OF THE INVENTION

This invention relates generally to treatment of carpal tunnel syndrome, and more particularly to a non-invasive apparatus and method for treatment of carpal tunnel syndrome.

BACKGROUND OF THE INVENTION

Carpal tunnel syndrome is a physiological disorder that afflicts over 850,000 people each year in the United States alone. In order to better understand the cause of the carpal tunnel syndrome and the difficulty in treating this serious disorder, a detailed explanation of the physiological factors and causes of carpal tunnel syndrome is presented below. Carpal tunnel syndrome is caused by a deleterious increase in pressure on the median nerve which passes through the carpal tunnel (or canal) in the hand, adjacent to the wrist. The deleterious increase in pressure, which is commonly brought on by prolonged repetitive motion of the hand and digits, is often caused by inflammation or damage to tendons for the hand which pass through the carpal tunnel along with the median nerve. Pressure increases can also be caused by narrowing of the carpal canal and by generalized swelling of the structures in the hand. Thus, when the carpal tunnel is narrowed from ligament shortening, muscle development or structural inflammation, the median nerve is undesirably compressed.

The carpal tunnel is formed by the eight carpal bones of the hand adjacent the wrist, which bones are arranged in two rows forming a generally U-shaped inverted arch-like "tunnel" structure. The three large carpal bones of the proximal row (i.e., closest to the chest), beginning laterally (i.e., from the outside with the hand directed downward and the palm facing forward), are the scaphoid, lunate, and triquetrum; the smaller pisiform bone sits on the palmar surface of the triquetrum. The distal row, from lateral to medial, consists of the trapezium, trapezoid, capitate, and hamate carpal bones. The vault of the carpal tunnel is formed by the carpal ligament and the flexor retinaculum. Nine tendons, their tendon sheaths, and the median nerve pass through the tunnel.

The carpal ligament is made of collagen and elastin and extends from the pisiformis and hamulus of hamate bones on the ulnar aspect of the tunnel to the tubercle (i.e., projection) of trapezium and the tubercle of the scaphoid bones on the radial (i.e. lateral) aspect of the carpal tunnel. The flexor retinaculum also stretches across the carpal tunnel and attaches to, on the medial aspect of the carpal tunnel, the pisiform bone and the hook of hamate, and, on the lateral aspect, the tubercle of the scaphoid and trapezium bones. The proximal border of the flexor retinaculum corresponds generally to the transverse skin crease at the base of the hand/wrist. The carpal ligament and flexor retinaculum, along with the carpal bones, form the restricted space through which the median nerve and several tendons pass.

Symptoms of carpal tunnel syndrome include tingling sensation in the hand, discomfort, numbness, and pain localized in the hand or radiating up the arm to the shoulder. All of these symptoms can occur during the day or can make the patients wake up at night. In advanced cases, there is atrophy and weakness of the thenar area of the hand which may weaken the grip and cause objects to fall out of the hand.

Conventional treatment of carpal tunnel syndrome is divided into surgical (invasive) and conservative (non-invasive). Surgical treatment consists of making an incision on the palmar aspect of the hand and splitting the carpal ligament, thus partially opening the carpal tunnel and relieving the pressure. This procedure, while occasionally successful, often has negative consequences, which include, but are not limited to, non-resolution of symptoms often requiring a second surgery, pain in the area of the scar, and injury to the superficial palmar branch of the median nerve causing persistent neurologic symptoms such as loss of full control over the hand. Furthermore, this procedure is very expensive. Understandably, surgical treatment is often considered as a last option.

Conservative, non-invasive treatment is typically separated into three categories—mild, moderate and alternative. Mild treatments may involve the use of anti-inflammatory medications, application of resting hand splints, physical therapy, modification of patient's activities that cause the condition, and even a change in the patient's job. Moderate treatments involve one or more mild treatments coupled with cortisteriod injections. Finally, alternative methods include acupuncture, massage, application of magnets, tai-chi exercises, and the like.

However, none of the above treatments have produced uniformly positive results. While some treatments may alleviate the symptoms of carpal tunnel syndrome in individual patients, the symptoms often return when the course of treatment is terminated. Furthermore, one of the main disadvantages of the various treatment approaches is that they must be delivered by a healthcare provider such as a physician or a physical or occupational therapist. This adds a significant level of inconvenience to the patient who must allocate time to visit the healthcare provider for injections and/or physical therapy. Medications that are used to provide relieve from the pain and discomfort caused by carpal tunnel syndrome also suffer from a number of disadvantages. For example, certain medications have undesirable side effects or interactions with the patient's other medications, if any.

As a result, a number of techniques for treating carpal tunnel syndrome that address at least some of the above problems have been developed over the years. Some merely maintain the patient's hand in a neutral position (such as the device disclosed in U.S. Pat. No. 5,014,689) to prevent the symptoms from worsening. Another approach involved mechanical stretching of the carpal ligament, as disclosed in U.S. Pat. No. 5,256,136. Yet another series of techniques advocated placement of a compression bracelet on the forearm (U.S. Pat. No. 5,441,058), or on the wrist (U.S. Pat. No. 5,468,220) to apply a predetermined pressure on certain portions of the forearm, or wrist, respectively, in order to widen the carpal tunnel and thus provide relief to the patient suffering from carpal tunnel syndrome.

However, the above-described previously known devices suffer from a crucial disadvantage. Application of pressure to different portions of the forearm and/or the wrist only has a minimal effect on widening the carpal tunnel, and may only provide temporary relief from carpal tunnel syndrome rather than eliminating or suppressing the condition.

Further development in the area of mechanical treatment of carpal tunnel syndrome continued, and eventually resulted in discovery of the Porrata principle, disclosed in the commonly assigned U.S. Pat. No. 6,146,347 to Humberto Porrata, that provides a novel and advantageous device and method for treating carpal tunnel syndrome that solve the problems posed by previously known devices and techniques. Most importantly, research conducted in conjunction with development of the Porrata device, has shown that carpal tunnel syndrome may be treated with great effectiveness by precise controlled transverse stretching of the carpal ligament and the flexor retinaculum. The U.S. Pat. No. 6,146,347 disclosed a splint-like device that fit over the patient's hand and a portion of the wrist. The device included rigid sections for contacting the thenar and hypothenar portions of the hand and a selectable active pressure source that, when actuated, applied pressure to the dorsal portion of the patient's hand opposed by the forces delivered by the thenar and hypothenar sections of the device in such a manner, as to transversely stretch the carpal ligament and the flexor retinaculum in a comfortable and controlled manner.

Nevertheless, the device of the U.S. Pat. No. 6,146,347 is susceptible to improvement. Because of its construction, it generally must be fabricated in different sizes to fit various patients, and patients with unusual hand sized or shapes may need custom-fabricated devices.

It would thus be desirable to provide an apparatus and method for treating carpal tunnel syndrome by stretching the carpal ligament and the flexor retinaculum of a patient's hand in a comfortable and controlled manner. It would further be desirable to provide an apparatus and method for treating carpal tunnel syndrome embodied in a device that is dynamically adaptable to patients of various physical characteristics.

SUMMARY OF THE INVENTION

The apparatus and method of the present invention advantageously overcome the problems and drawbacks of previously known approaches for treating carpal tunnel syndrome. Similarly to the device disclosed in the commonly assigned U.S. Pat. No. 6,146,347 which is hereby incorporated by reference in its entirety, the main objective of the present invention is to apply the Porrata principle to stretch the carpal ligament and the flexor retinaculum, as well as the superficial structures and muscles of the hand, in a safe manner under precise control of the patient or a healthcare professional. However, the apparatus and method of the present invention enable the Porrata principle to be implemented in a device that may be readily used by patients with any size or shape hands. Furthermore, the inventive apparatus is very simple and inexpensive to manufacture.

Controlled and monitored use of the inventive apparatus dynamically treats carpal tunnel syndrome through the controllable selective application of pressure to large portions of the palm of the hand (in the thenar and hypothenar areas) while at the same time retaining the central dorsum of the hand, in essence providing pressure in the opposite direction. Alternately, active pressure is selectively applied to the central dorsum of the hand as well. This procedure transversely stretches the carpal ligament, the flexor retinaculum, and superficial structures and muscles of the hand in the palmar aspect of the hand, in a readily, safely controllable and comfortable manner.

Considering that the constitutions of the carpal ligament and the flexor retinaculum are soft tissue composed of collagen and elastin, transverse stretching of the carpal ligament and the flexor retinaculum is effective for decreasing compression on the median nerve by increasing the diameter of the tunnel and decreasing the rigidity of the retinaculum and the carpal ligament, thus alleviating the symptoms of carpal tunnel syndrome.

Various embodiments of the inventive apparatus commonly include a housing for receiving the patient's hand with a bottom portion having a first pressure element adapted and configured to contact the hypothenar region of the patient's hand, a second pressure element adapted and configured to contact the thenar region of the patient's hand, and a top portion having a central longitudinal third pressure element adapted and configured to contact the central longitudinal dorsal region of the patient's hand. In a first embodiment of the present invention, the first and second pressure elements are connected to active pressure sources (or source), such that when the hand is inserted into the housing, the first and second pressure elements are activated and exert pressure on the respective hypothenar and thenar regions of the hand, while the central dorsal portion of the hand presses against the third pressure element. This forces the thenar and hypothenar regions apart, thus advantageously stretching the carpal ligament, the flexor retinaculum, and superficial structures and muscles of the hand. In another embodiment of the present invention, the third pressure element is also connected to an active pressure source, such that active pressure is applied to the central dorsal region of the hand while the first and second pressure elements apply pressure to the hypothenar and thenar regions of the hand.

Because the various pressure elements are adjustable and configurable (by varying the magnitude of pressure delivered by the pressure sources), the inventive apparatus is readily usable by patients with different hand shapes and/or sizes to prevent progression of carpal tunnel syndrome and to provide relief from symptoms by increasing the cross sectional area of the carpal tunnel, thus decreasing compression on the median nerve and decreasing the resulting symptoms.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. dr

BRIEF DESCRIPTION OF THE DRAWINGS

In the drawings, wherein like reference characters denote like elements throughout the several views.

DETAILED DESCRIPTION OF PREFERRED EMBODIMENTS

The present invention is described with reference to various materials that compose the inventive structures and elements thereof, and to various devices for selectively applying pressure to specific areas of the hand, by way of example only—it should be understood that the apparatus and method of the present invention may be utilized with any materials or selective pressure sources having properties similar to those described in the exemplary embodiments, without departing from the spirit of the invention.

The essence of the Porrata approach, disclosed and described in greater detail in the above-incorporated U.S. Pat. No. 6,146,347, involves applying pressure to a portion of the top surface of the hand (i.e., the central dorsal region), while at the same time applying opposing pressure to the thenar and hypothenar regions of the palm. The apparatus and method of the present invention advantageously implement the Porrata principle in a simple to use device that works equally well with different hand shapes and sizes.

Figure 1:
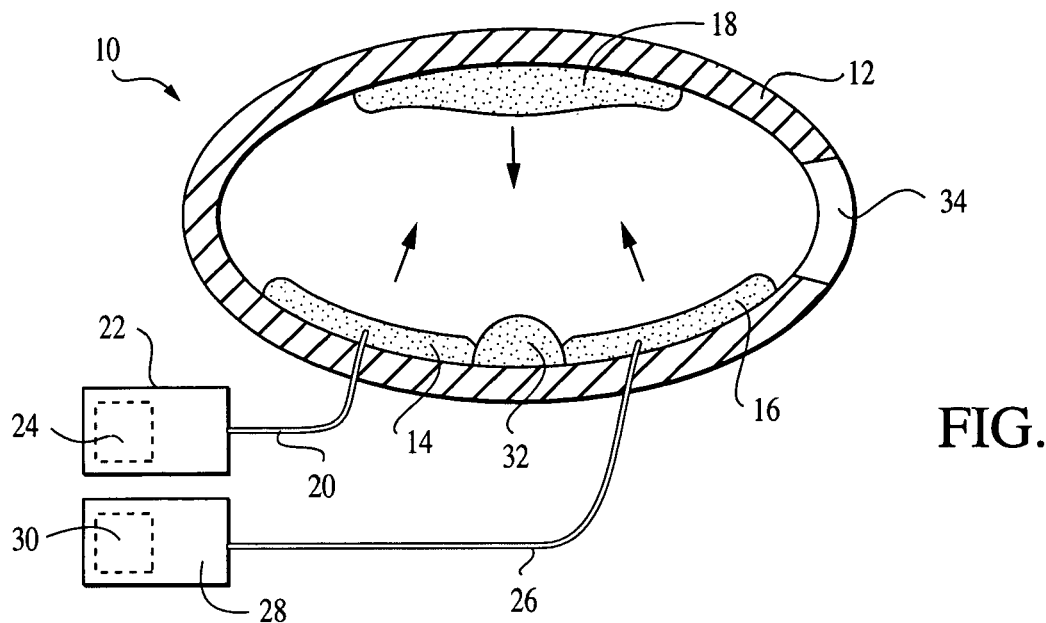
FIG. 1 is a cross-section view of a first embodiment of the inventive apparatus for treating carpal tunnel syndrome.

Referring now to FIG. 1, a first embodiment of an inventive apparatus 10 is shown. The apparatus 10 includes a housing 12 having an internal hollow region, an internal central top portion having a first central longitudinal section, an internal bottom portion having a second longitudinal section and a parallel third longitudinal section, and an open end portion for receiving the hand into the internal region such that the hypothenar region of the hand is substantially aligned with said first section, and the thenar region of the hand is substantially aligned with said second section. The housing 12 also includes a first active pressure element 14 for contacting the hypothenar region of the hand, a second active pressure element 16 for contacting the hypothenar region of the hand, and a pressure member 18 for contacting the longitudinal central dorsal portion of the hand. The housing 12 may be composed of a rigid material such as metal, hard plastic or wood, or a resilient material such as fiberglass or resilient plastic, or a combination thereof. Optionally, the housing 12 may include a plurality of ventilation openings (not shown) to provide ventilation to the patient's hand during the operation of the apparatus 10. The housing 12 may also include an optional hole 34 in a side wall thereof for receiving the patient's thumb. The housing 12 may also include an optional heat source 32 disposed between the first and the second active pressure elements 14, 16 for applying heat to the patient's palmar region during therapeutic use of the apparatus 10 to aid in stretching the ligaments of the hand. The pressure member 18 may be composed of any rigid or resilient material, or a combination thereof.

The first active pressure element 14 is connected to a first pressure source 22 via a connector 20, while the second active pressure element 16 is connected to a second pressure source 28 via a connector 26. The first and second pressure sources 22, 28 may include optional pressure indicators 24, 30, such as, for example, pressure gauges, digital indicators, or release valves set to certain pre-determined pressures. Alternately, the first and second pressure sources 22, 28 may be positioned proximal to the outer surface of the housing 12, and directly connected to the respective active pressure elements 14, 16 without the use of the respective connectors 20, 26.

The first and second active pressure elements 14, 16 may be any variable (singular or plural) pressure elements such as air or fluid inflatable bladders, mechanical pressure plates, electromechanical pressure plates, or a combination thereof. The first and second pressure sources 22, 28 (and the connectors 20, 26) are selected to correspond to the respective first and second active pressure elements 14, 16 to provide the necessary pressure control. For example, if the first and second active pressure elements 14, 16 are air-inflatable bladders, the first and second pressure sources 22, 28 are air pumps (and the connectors 20, 26 are air hoses). In this example, control over the delivered pressure is actuated by air release valves. In another example, if the first and second active pressure elements 14, 16 are mechanically actuated plates, the first and second pressure sources 22, 28 are screw, puller or wedge mechanisms disposed on the housing 12. In this example, control over the delivered pressure is actuated by rotating the screw or puller mechanism(s), or by moving the wedge(s). In yet another example, if the first and second active pressure elements 14, 16 are electromechanically actuated plates (for example, using electromagnets), the first and second pressure sources 22, 28 are electrical power sources (and the connectors 20, 26 are wires). In this example, control over the delivered pressure is actuated by varying the electrical power delivered by the electrical power sources. Other types of active pressure elements, and corresponding pressure sources, may be utilized as a matter of design choice without departing from the spirit of the present invention. Optionally, both pressure sources, 22, 28 may be embodied in a single unit for actuating both active pressure elements 14, 16.

To utilize the apparatus 10, a patient inserts their hand into the housing 12, such that the first active pressure element 14 contacts the hypothenar region of the palm and the second active pressure element 16 contacts the thenar region of the palm, while the pressure member 18 contacts the longitudinal central dorsal region of the hand. The pressure sources 22, 28 are then activated, causing the active pressure elements 14, 16 to deliver upward pressure on the respective hypothenar and thenar regions of the hand, while the pressure member 18 retains and presses downward against the central dorsal region. The first and said second upward forces are thus opposed by the downward force exerted by the pressure member 18 on the central dorsal region of the hand, such that the downward force is balanced and opposed by the first and second upward forces causing carpal bones of the hand to separate to transversely stretch the carpal ligament and the flexor retinaculum of the hand, thus implementing the Porrata principle to widen the carpal canal and provide treatment of carpal tunnel syndrome to the patient. The inventive apparatus 10 is advantageous because the size of the active pressure elements 14, 16 is controllable by the user—thus the apparatus 10 may be utilized by patients having varying hand shapes and sizes. The amount of pressure applied by the active pressure elements 14, 16 is also preferably controllable by the user and may be set to a predetermined amount based on an evaluation by the user's physician or therapist.

Figure 2:
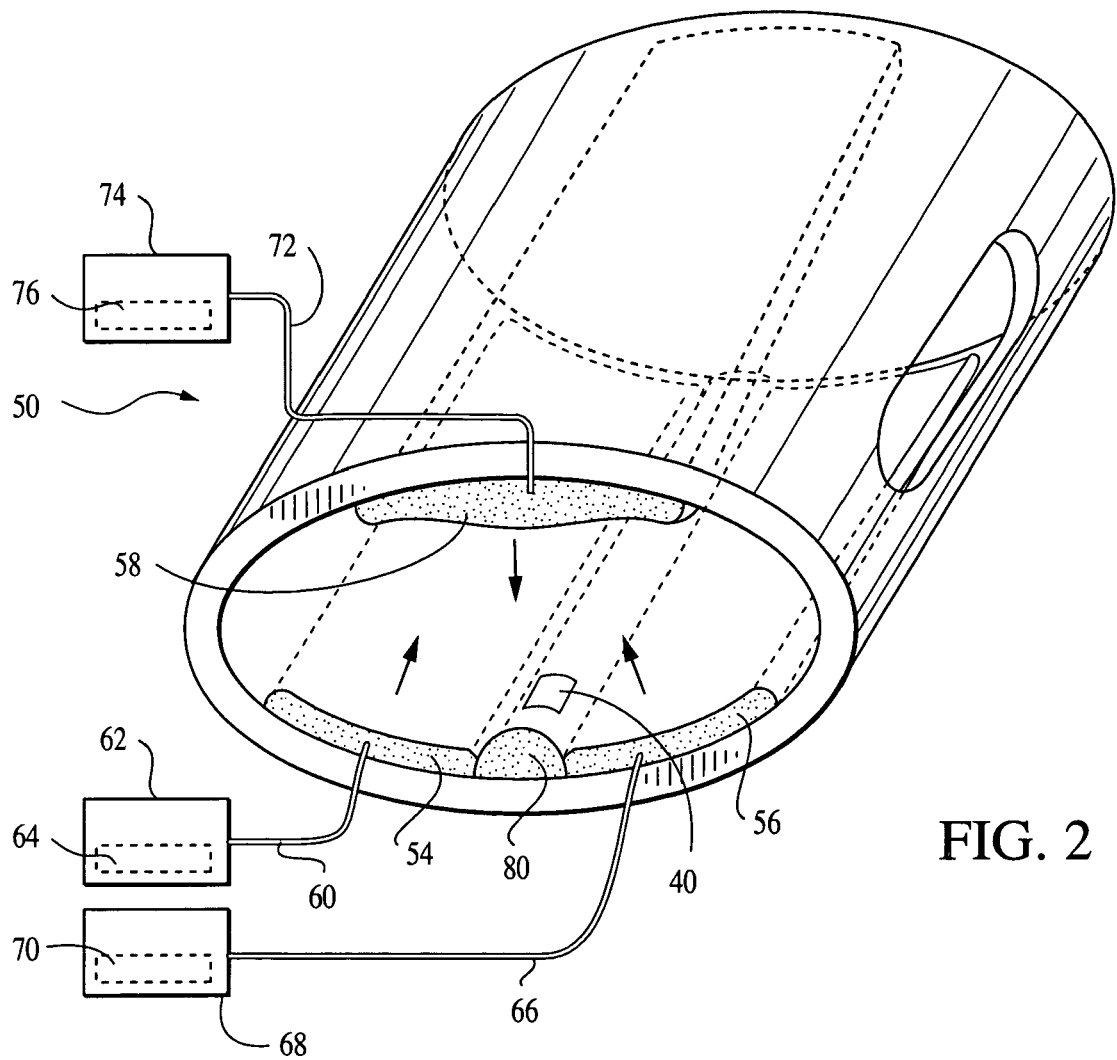
FIG. 2 is an isometric top view of a second embodiment of the inventive apparatus for treating carpal tunnel syndrome.

Referring now to FIG. 2, a second embodiment of the inventive apparatus is shown as an apparatus 50. The apparatus 50 operates in a substantially similar manner to the apparatus 10, except that the pressure member 18 is replaced by an active pressure element 58 connected to a third pressure source 74 via a connector 72. During utilization of the apparatus 50, instead of a fulcrum-like passive pressure caused by the pressure member 18 of apparatus 10 of FIG. 1, the active pressure element 58 is actuated by the third pressure source 74 to selectively deliver pressure to the longitudinal central dorsal region of the hand. The three active pressure elements, including active pressure element 58, may also be actuated by a single or combined pressure source as previously described.

FIG. 2 also shows that the apparatus 50 may also include an electronic device 40 that includes a laser or similar device adapted to specifically denature the proteins that make up the ligaments in the body, thus making it easier to stretch the ligaments. The electronic device 40 is preferably aligned with the flexor retinaculum or carpal ligament as the hand is placed in the apparatus 50. The electronic device 40 may also include conventional sensors to measure the amount of stretching or elongation of the flexor retinaculum or carpal ligament through, e.g., tension measurements or displacement of carpal bones.

Thus, while there have been shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. An apparatus for treating carpal tunnel syndrome in a person's hand, the hand having a longitudinal axis, a palmar aspect with thenar and hypothenar regions and a dorsal region opposed to the palmar aspect, the apparatus comprising a tubular housing having an internal hollow region, a first adjustable pressure member located on a lower portion of the hollow region, a second adjustable pressure member located on the lower portion of the hollow region adjacent said first pressure adjustable pressure member, a third adjustable pressure member located on an upper portion of said hollow region, said first adjustable pressure member, said second adjustable pressure member and said third adjustable pressure member each extending along a substantial portion of said hollow region, a means for heating located between said first adjustable pressure member and said second pressure adjustable member, a first means for adjusting the first adjustable pressure member, a second means for adjusting the second adjustable pressure member and a third means for adjusting the third adjustable pressure member, a means for measuring the amount of stretching or elongation of the carpal ligament, said first adjustable pressure member is sized and configured to apply pressure to the hypothenar region, the second adjustable pressure member is sized and configured to apply pressure to the thenar region and the third adjustable pressure member is sized and configured to apply pressure to the central dorsal region of the hand.

2. The apparatus of claim 1, wherein the first and second pressure adjustable members comprise a pressure indicator.

3. The apparatus of claim 2, wherein said tubular housing further comprises an opening configured and positioned to receive a thumb of the hand.

4. The apparatus of claim 3, said first and second pressure adjustable members include a pressure indicator.

5. The apparatus of claim 4, further comprising a laser adapted to denature proteins forming the flexor retinaculum and carpal ligament.

* * * * *